US 6,570,395 B2

(12) United States Patent
Falbo et al.

(10) Patent No.: US 6,570,395 B2
(45) Date of Patent: May 27, 2003

(54) PORTABLE GRAIN MOISTURE METER

(75) Inventors: James T. Falbo, Stow, OH (US); John W. Dubay, Chagrin Falls, OH (US); Trent A. McElhaney, North Jackson, OH (US)

(73) Assignee: Worens Group Inc., Sarasota, FL (US)

( * ) Notice: Subject to any disclaimer, the term of this patent is extended or adjusted under 35 U.S.C. 154(b) by 0 days.

(21) Appl. No.: 09/920,916

(22) Filed: Aug. 2, 2001

(65) Prior Publication Data

US 2003/0025513 A1 Feb. 6, 2003

(51) Int. Cl.$^7$ .............................. G01R 27/26; G01N 5/02
(52) U.S. Cl. ........................ 324/664; 324/665; 324/670; 73/73
(58) Field of Search ................................. 324/664, 666, 324/670, 686, 689, 71.1, 665; 460/7; 73/73, 818

(56) References Cited

U.S. PATENT DOCUMENTS

| 4,139,069 A | * | 2/1979 | Domis et al. ................ 177/1 |
| 4,326,542 A | * | 4/1982 | Laszlo et al. .............. 131/280 |
| 5,106,339 A | * | 4/1992 | Braun et al. .................. 460/7 |
| 5,487,702 A | * | 1/1996 | Campbell et al. ........... 34/484 |
| 5,663,650 A | * | 9/1997 | McMahon ................. 324/664 |
| 5,957,773 A | * | 9/1999 | Olmsted et al. ........... 460/149 |

\* cited by examiner

Primary Examiner—N. Le
Assistant Examiner—Anjan K. Deb
(74) Attorney, Agent, or Firm—Vytas R. Matas

(57) ABSTRACT

A portable grain moisture measurement device has an automatic grain moisture measurement actuation system whenever the compaction of the grain within a test cell of the device is at a preset value and upon such automatic actuation a visual display is activated to indicate that a moisture measurement is being taken as well as the sounding of an audible alarm indicating this measurement to warn the user that further compaction of the grain is unnecessary.

11 Claims, 6 Drawing Sheets

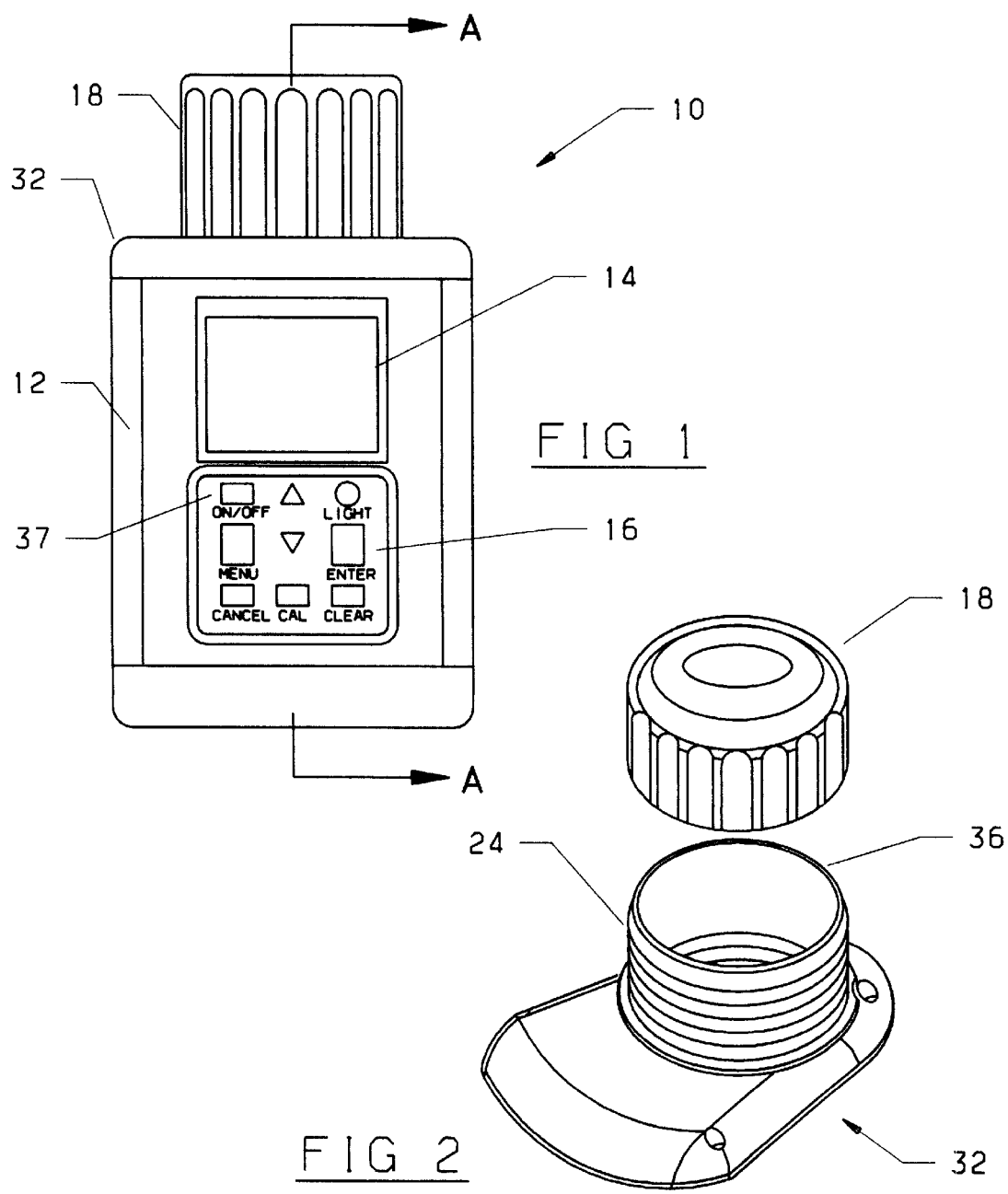

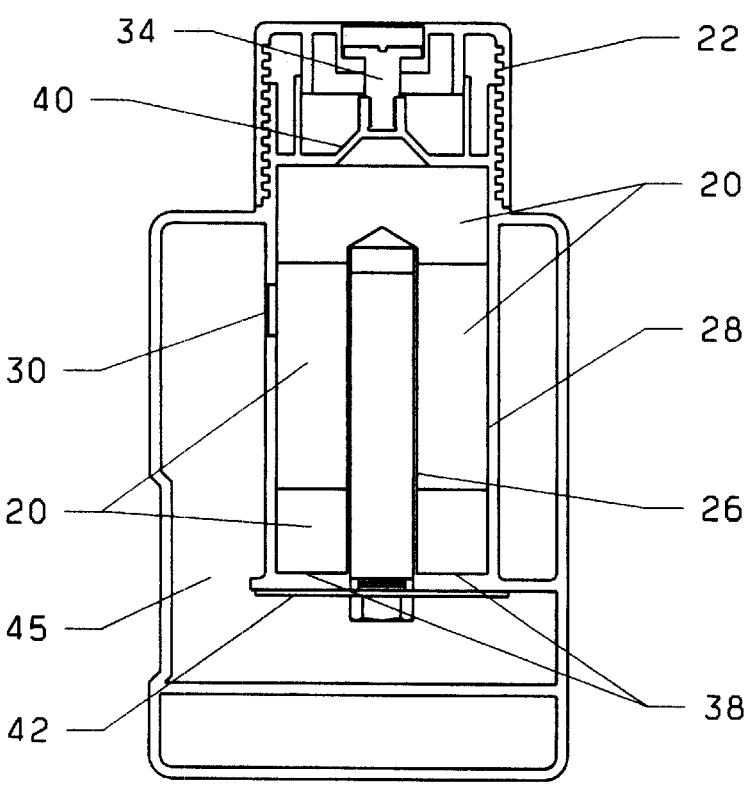
FIG 3
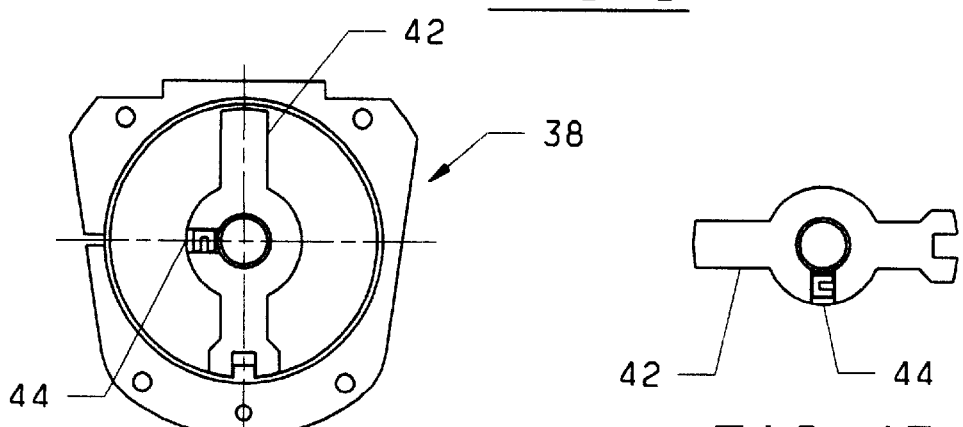
FIG 4A
FIG 4B

PORTABLE GRAIN MOISTURE METER

BACKGROUND OF THE INVENTION

1. Field of the Invention

This invention relates generally to portable testers for measuring the water content of a material using a measurement of the dielectric constant of the material and particularly to such testers, which measure the moisture content of a predetermined repeatable volume of grain.

2. Description of the Prior Art

There have previously been several ways to compensate for how the grain sits in the test cell or a means to account for the grain density to increase the moisture measurement accuracy. The early prior art grain moisture meters, both portable and commercial, neither used preset compaction nor weighing of the grain to allow for density variation compensation. The lack of these compensations limited the accuracy in their moisture measurements.

Later commercial testers weighed the grain in the test cell for density compensation. However, this form of density compensation is not easily incorporated into small portable moisture measuring devices and is impractical for such devices. Weighing grain, nevertheless, today is a known method for large on site commercial moisture testers to compensate for grain density variations.

Compaction is used to determine grain moisture as shown in U.S. Pat. No. 3,890,830, which utilized a compaction method for determining the grain moisture. However, this technique provides no measurement of the dielectric constant of the grain after compaction. Not obtaining the dielectric constant measurement in conjunction with the compaction measurement results in an unacceptable error when determining the grain moisture content. It also fails to provide a preset compaction trigger point to determine when the grain in the test cell is properly compacted and ready for the dielectric constant measurement.

Another known portable moisture tester using density, or compaction control is found in U.S. Pat. No. 5,663,650. It used a spring-loaded cap with a plunger inside of it. The procedure involved placing grain in the test cell and screwing down the cap until a detent, in the middle of the cap, became flush with the top of the cap. After the detent was flush, the user would then manually press the TEST button to obtain the moisture content. While a useful and valid approach for grain compaction repeatability, this device left it to the users discretion to determine when the cap detent was flush with the top of the cap before testing dielectric constant of the grain in the test cell. The users estimation of the flushness of the detent with the top of the cap is a subjective judgment and introduced errors. This human intervention did not allow for an automatic moisture reading trigger point since the user makes the detent flush then manually presses the test button to measure the grain's dielectric constant. Also, this method made it the responsibility of each user to determine when the detent is indeed flush with the cap. This resulted in measurement variations and error from one user to the next.

In view of the forgoing it will be seen that the prior art portable grain moisture measurement devices did not provide a density dependent automatic moisture measurement trigger point which was repeatable and error free from user to user.

SUMMARY OF THE INVENTION

The present invention provides a portable grain moisture-measuring device having a means of measuring the compressive force of the grain in a test cell of the device via a strain gage-bending arm on the bottom of the test cell. The signal from the strain gage is compared to a preset signal of desired force to automatically take the grain moisture measurement at the same amount of grain compaction for each successive test. The strain gage is in a full Wheatstone bridge configuration with the differential output of the bridge amplified by a gain of 1000 to obtain a reasonable resolution for a device microprocessor used to operate the automatic testing triggering and other measurements.

When using the device, the test cell is filled directly by the user. After that the user simply threads the cap and stops turning the cap when the tester beeps and displays TESTING. This indicates the preset force on the grain has been achieved and testing measurements have been initiated. If the user continues to screw down the cap, after the beep, this does not produce any error since the dielectric constant reading immediately follows the strain gage trigger point, within milliseconds.

The present device uses a firmware algorithm that first determines the unloaded strain level and then continuously measures the strain, as the cap is threaded. Once the measurement reaches the preset difference from the initial strain the tester knows it is at the same compaction level as when the grain was originally calibrated in the test cell. This results in a more repeatable measurement.

The device of the present invention uses measurements of compaction, temperature, and dielectric constant to obtain the grain moisture. More specifically, it uses a preset compaction trigger point to determine when the grain in the test cell is ready for the above measurements including the dielectric constant measurement. The automatic trigger point is preset and is proportional to the amount of compression on the grain within the filled test cell. This preset automatic triggering of testing allows the moisture meter to identify the correct time to make repeatable error free measurements including the dielectric constant of the grain filled test cell. This trigger point is preset to be the same point used when calibrating the testers memory for different grains to provide programmed grain moisture calibration curves. This results in repeatable moisture readings each time the grain moisture meter is used even by different people.

In view of the foregoing it will be seen that one aspect of the present invention is to provide a grain moisture-measuring device, which automatically initiates moisture-testing measurements at preset grain compaction levels.

Another aspect is to provide a repeatable moisture measurement between different tester users.

Yet another aspect is to provide a tester having a triggered moisture measurement at a preset compaction of a test cell, which is not affected, by further compaction of the cell.

These and other aspects of the present invention will be more fully understood upon a review of the following description of the preferred embodiment when considered in conjunction with the drawings.

BRIEF DESCRIPTION OF THE DRAWINGS

In the drawings

FIG. 1 is a front view of the portable grain moisture tester of the present invention;

FIG. 2 is a top perspective view showing the screw down cap of the test cell and the top of the FIG. 1 tester;

FIG. 3 is a cutaway view of the FIG. 1 tester taken along section A—A.;

FIG. 4A shows the bending arm, mounted in the bottom of the test cell, used for the trigger point sensing in the FIG. 1 tester;

FIG. 4B shows the bending armand strain gage sensor used for the trigger point sensing in the FIG. 1 tester;

DESCRIPTION OF THE PREFERRED EMBODIMENT

Figure 5:
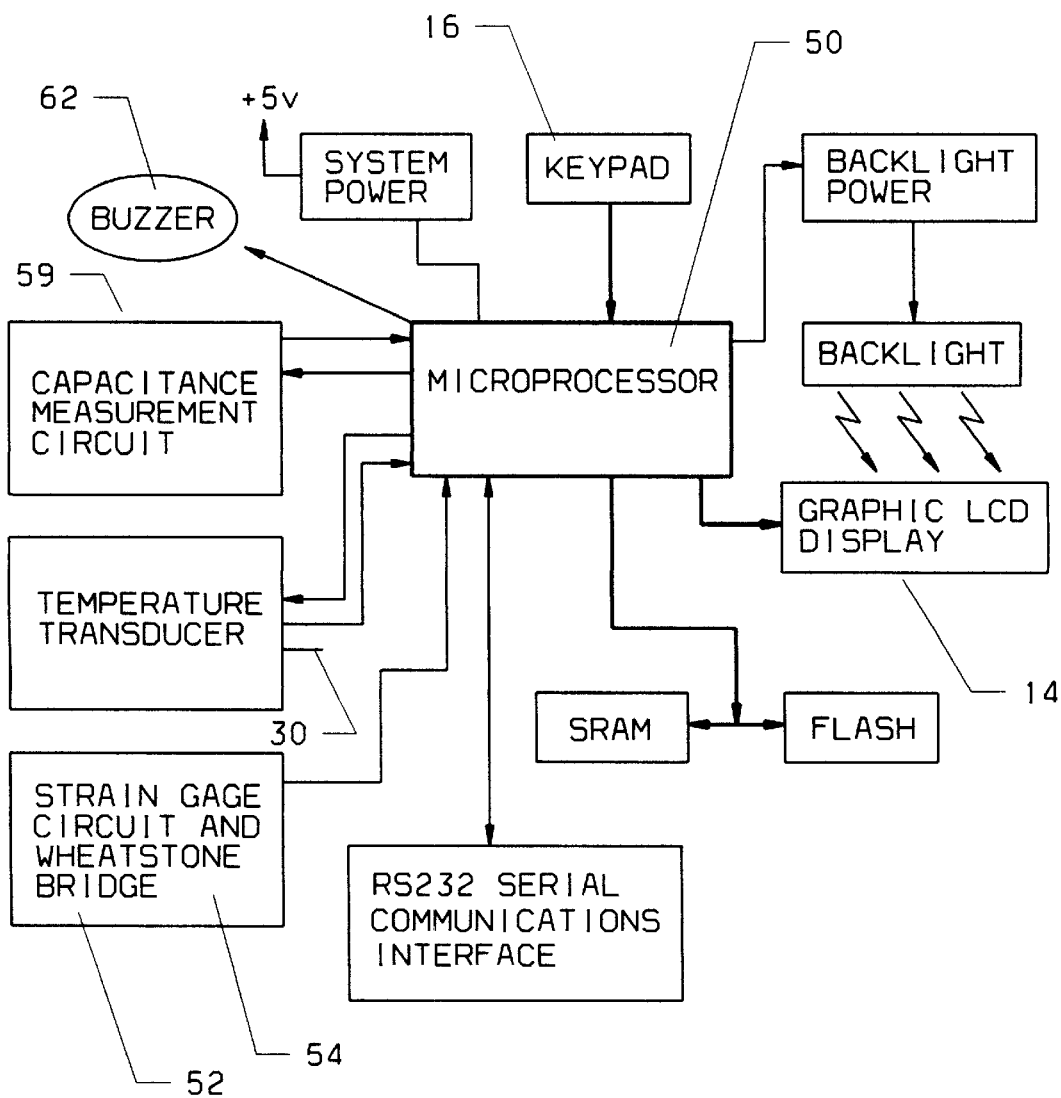
FIG. 5 is a block diagram of the electronic circuitry used by the FIG. 1 tester.

Turning now to the drawing where the showings are intended to depict a preferred embodiment of the present invention but not limit the invention thereto, FIGS. 1–4 show a portable grain moisture meter (10) having a front face plate assembly (12) which includes a graphic LCD display (14) and a keypad (16) for user inputs.

The moisture meter (10) is a capacitive type grain moisture meter, which uses a constant grain volume as the capacitance dielectric material. The signal attenuation across the grain varies with moisture content of the dielectric and therefore is proportional to the grain moisture. Such a device is generally described in prior art U.S. Pat. Nos. 3,761,810 and 3,781,673 the contents of which are incorporated by reference and the reader is referred thereto for further details of the structure and operation of such devices.

In the grain moisture meter (10), a constant volume is provided by pouring grain into a test cell (20), all the way up to rim (36). As it is poured, grain falls between an inner (26) and an outer (28) electrode filling the cell (20). The test cell (20) has a temperature transducer (30) bonded to the outer electrode (28) via thermal epoxy. The grain temperature compensation utilizes this transducer to adjust grain moisture readings accordingly.

Referring more particularly to FIGS. 2–3, the test cell (20) is shown to have a cap (18) having inside threads (22), which mate to outer surface threads (24) formed in the top section (32) of the tester (10). The cap (18) contains a plunger plate (40), which is slightly smaller than the diameter of the test cell (20) and is used to compress the grain sample in the test cell (20) as the cap (18) is screwed on to the threaded top portion (24) of the tester.

Referring particularly to FIG. 3 it will be seen that the plunger (40) is threaded onto a screw (34) extending through the cap (18) by complementary threads on the screw (34) and the plunger (40). The plunger (40) exerts pressure on the grain in the test cell (20) of increasing magnitude as the cap (18) is threaded on to the outside threads (24) of the top of the tester (32).

Figure 6A:
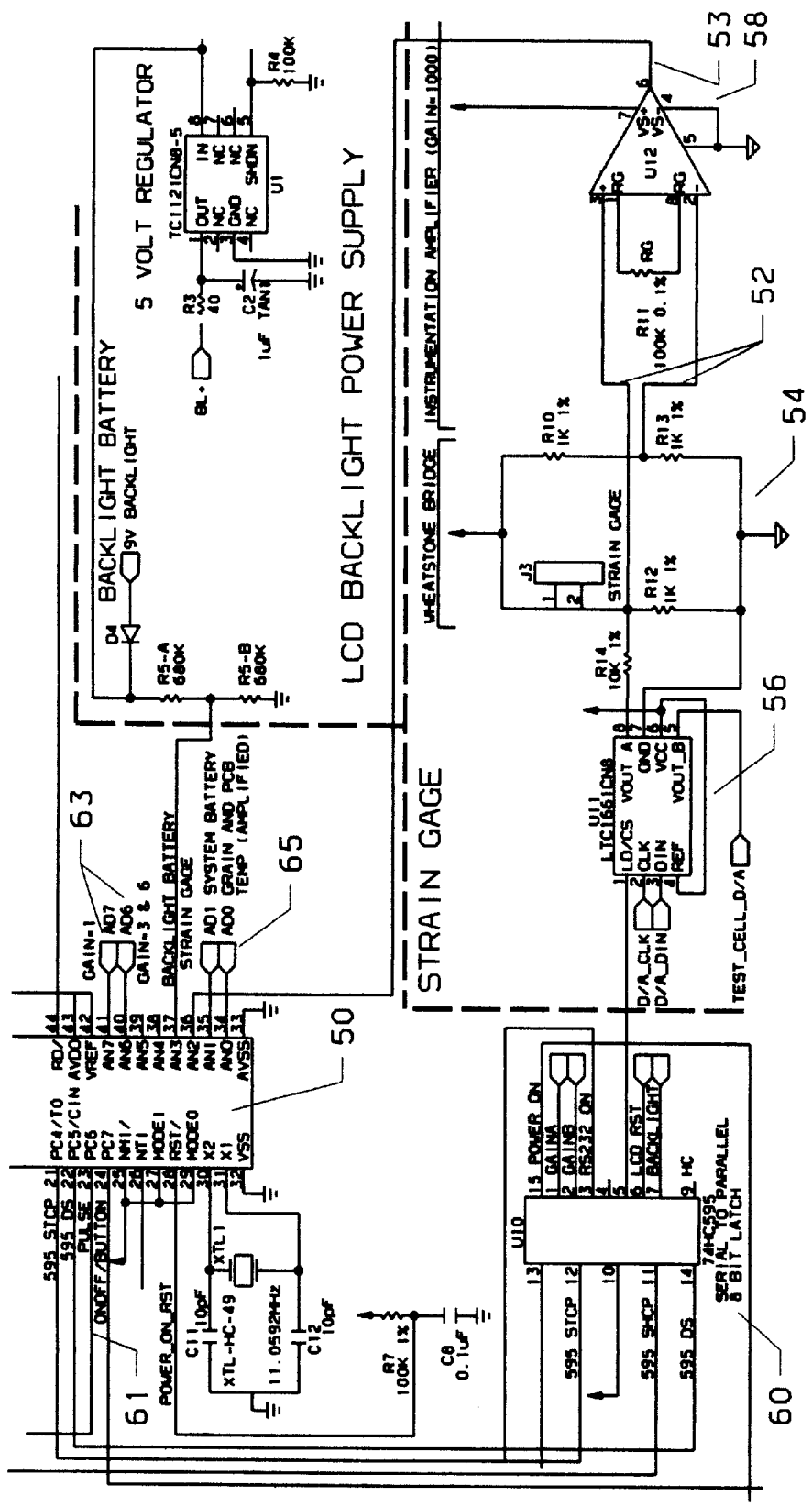
FIGS. 6A,6B,6C are schematics of the circuitry used by the strain gage circuitry, the capacitance measuring circuit and the buzzer of the FIG. 1 tester.
Figure 6B:
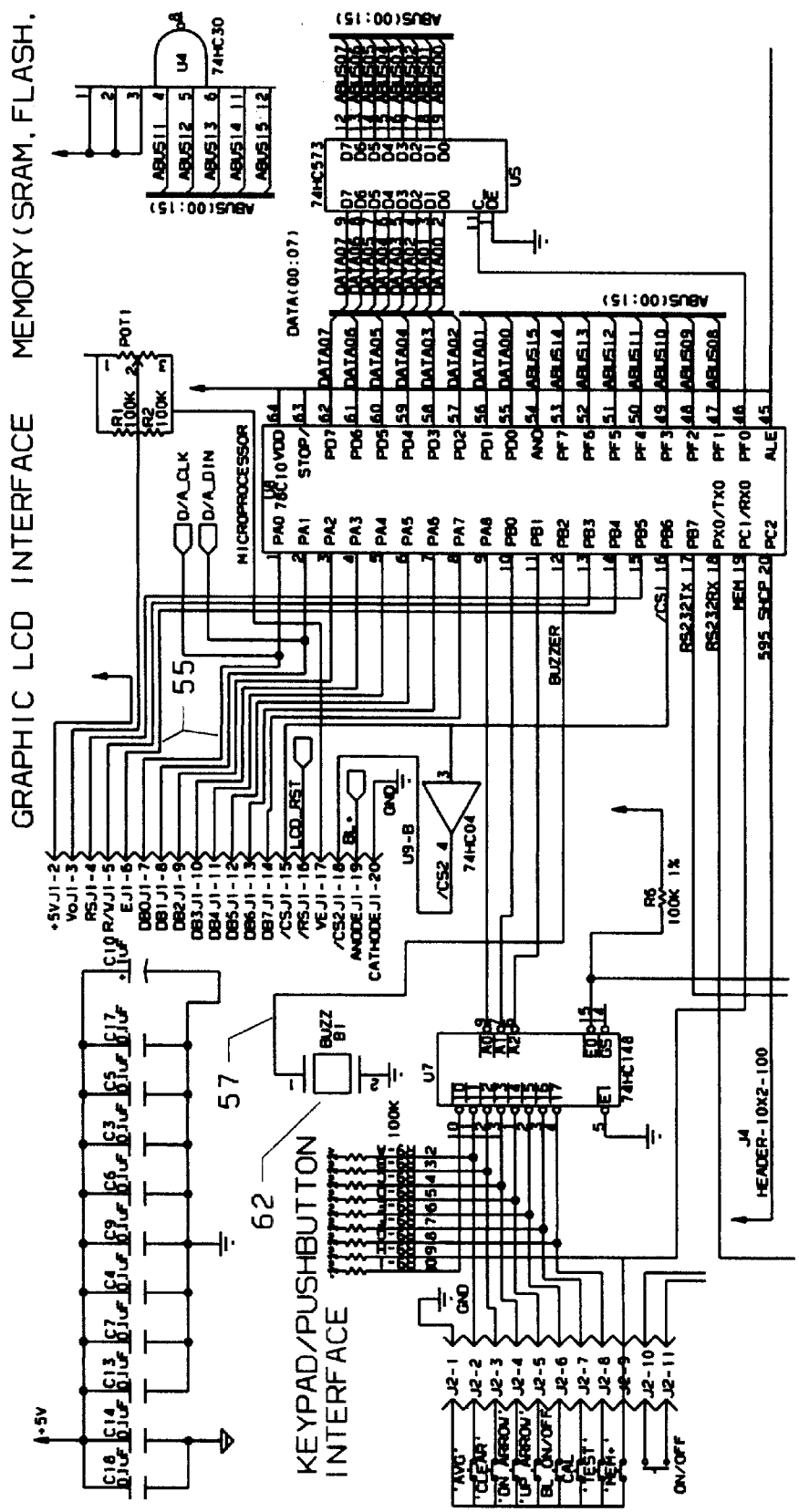
Figure 6C:
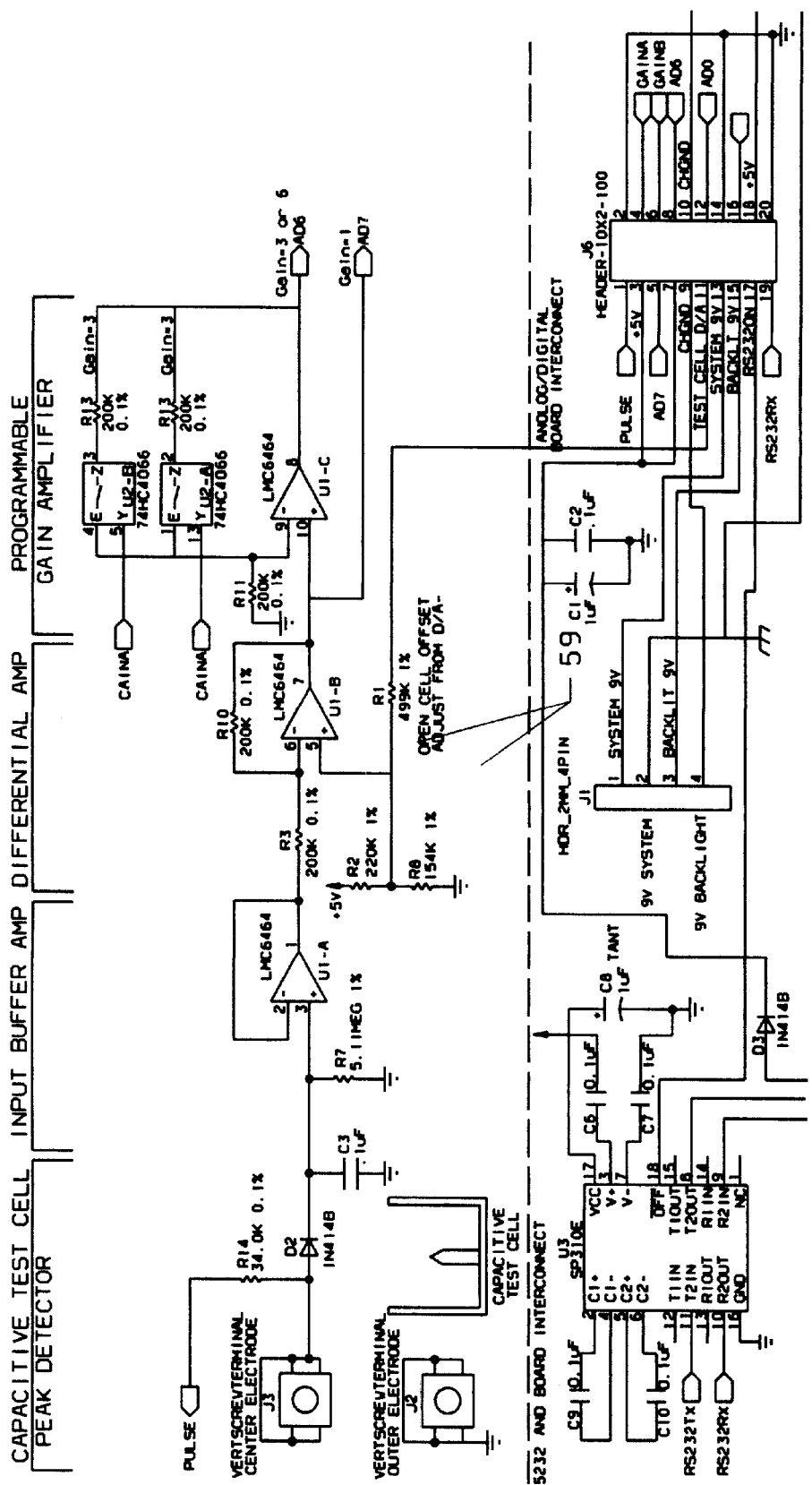

Referring now to FIGS. 5–6, the electronic circuitry located internally in a cavity (45) of the tester(10) which co-ordinates and records the measurements taken by the tester (10) to display a grain moisture content on the readout display (14) of the tester (10) will be explained.

To initiate a moisture measurement, the user first turns the tester (10) on by depressing an on/off switch (37) located on the keypad (16). The user then removes the cap (18) and pours grain into the test cell (20) and fills it to the rim (36). During this fill period a microprocessor (50) reads the output value of a strain gage bridge circuit (52) connected to the microprocessor (50) by line (53). As the grain is being poured into the cell (20) the microprocessor (50) monitors the change in dielectric constant within the cell (20) in a known manner. The initial value of the strain gage, also known as the unloaded strain value was saved by the microprocessor (50) as a value stored in ROM.

The user upon filling the test cell (20) places the cap (18) on the tester (10) and begins to screw it down. The microprocessor (50) reads the strain gage (44) compression value and compares it to a set point value stored in ROM. When the compression value changes a predetermined amount from the unloaded strain value reaching the loaded set point, the microprocessor (50) sends a signal to the LCD display (14) along line (55) to actuate a display thereon reading TESTING. The microprocessor also sends a simultaneous signal along line (57) to a piezoelectric buzzer (62) to actuate an audible signal lasting a few seconds. These signals alert the user that no further compaction is necessary since the readings for calciulating the moisture have been initiated. Reaching the set point compression value is the trigger point that initiates the microprocessor (50) to output a signal to a capacitance measuring circuit (59) along line (61) to read the dielectric constant of the grain in the test cell (20) using the electrodes (26,28) in a known manner and to send this value back to the microprocessor along line (63) to use this value to determine the moisture content in a known manner. Any further compaction of the grain by the user continuing to screw the cap (18) is ignored since the only value used for moisture calculation is this trigger value of the dialectric constant measurement. This repeatable trigger point takes moisture measurements with the same compaction applied to the grain each time independently of the user and his subjective opinion of proper compaction. This improves moisture reading repeatability over the prior art devices as described in U.S. Pat. No. 5,663,650 which required a user to subjectively identify proper compaction.

Simultaneously with the initial strain gage readings and successive readings up to the set point reading being obtained and stored, the bottom of the test cell (38) starts to flex after the cell is full and the user screws down the cap (18). Since the bending arm (42) is mounted flush with the bottom of the test cell (38) the strain gage (44) also flexes. This causes a change in strain gage resistance, which translates to a voltage difference at the output of the Wheatstone bridge (52). A gain of 1000 through Analog Devices Instrumentation opamp (58) amplifies this voltage difference. This amplified voltage is directly input to and digitized by the microprocessor (50) analog input port as shown in the block diagram (FIG. 5).

The Wheatstone bridge (54) must be balanced since the three resistors and the strain gage (44) are not ideal and all have some resistance tolerance associated with them. The resistors are 0.1% and the strain gage (44) is 0.3% tolerance. Linear Technologies LTC1661 digital to analog converter (56) is used for balancing the wheatstone bridge (54). This is a know method for balancing strain gage circuits. The microprocessor (50) adjusts the digital to analog converter (56), via a 74HC595 serial to parallel latch (60) and microprocessor (50) I/O lines, until the bridge is nulled. This nulled value is actually a predetermined value rather than a value of zero volts.

The microprocessor (50) also receives a signal along line (65) from the temperature trsansducer (30) mounted on the outside of test cell (20) to be used for compensating the moisture measurement for temperature in aknown manner.

From the foregoing it will be seen that the present tester automatically provides repeatable value moisture sensing based upon a repeatable compaction irrespective of different users and how much they continue to compact the device after moisture measurement is automatically initiated.

Certain modifications and additions have been deleted herein for the sake of conciseness and readability. As an example, details of the, construction and operations of well-known circuit elements are deleted. However, all such are intended to be included in the scope and understanding of the following claims.

What is claimed is:

1. A grain moisture measuring device providing an automatic grain moisture measurement at a preset compaction value comprising:
    an automatic grain moisture-measuring device;
    a test cell located within said measuring device for holding a predetermined grain volume therein when filled to the top with grain;
    a strain gage mounted to said test cell to determine the force compaction of the grain in said test cell;
    means for manually compacting the grain of predetermined volume within said test cell;
    means for comparing the strain gage output during the compacting of the grain by said manual compacting means to a preset value and stored in said comparing means and establishing a signal indicative of the difference there between; and
    means for automatically initiating an immediate moisture measurement by said moisture measuring device upon a signal from said comparing means indicating no difference between the preset value and the measured value by said strain gauge even if said manual compacting means is continuing the grain compaction.

2. A grain moisture measuring device as set forth in claim 1 wherein said means for compacting the grain in said test cell includes a threaded cap for said test cell having a member attached thereto which presses on the grain as said cap is screwed on to said test cell.

3. A grain moisture measuring device as set forth in claim 2 wherein said means for comparing strain gauge output comprises a microprocessor connected to an amplifier and to said strain gauge through a Wheatstone bridge.

4. A grain moisture measuring device as set forth in claim 3 wherein said means for initiating a moisture measurement includes a capacitance measuring circuit connected to said microprocessor for measuring the dielectric constant of the grain in said test cell.

5. A grain moisture measuring device as set forth in claim 4 including a graphic LCD display on the face of said moisture measuring device for displaying a TESTING logo whenever said moisture measurement is initiated.

6. A grain moisture measuring device as set forth in claim 5 including a buzzer in said moisture measuring device for sounding an audible signal whenever said moisture measurement is initiated.

7. A grain moisture measuring device as set forth in claim 6 wherein said moisture-measuring device is portable.

8. A method of automatically initiating a moisture measurement in a moisture measuring device upon detection of a preset compaction of grain within a test cell of the device comprising the steps of:
    filling the test cell with a predetermined volume of grain up to the top thereof;
    manually pressing the grain into the test cell to continually compress the grain therein;
    continuously measuring the compaction of the grain in the test cell during the manual compaction thereof;
    comparing the continuous compaction value with a preset value; and
    automatically initiating an immediate moisture measurement by the device when the compaction value reaches the preset value even if further manual compaction is continued.

9. A method of automatically initiating a moisture measurement in a moisture measuring device as set forth in claim 8 further includes the steps of sounding an audible signal whenever an automatic moisture measurement is initiated by the device to indicate no further compaction is needed.

10. A method of automatically initiating a moisture measurement in a moisture-measuring device as set forth in claim 8 further includes the steps of displaying a visible signal on a display area of the device indicating a moisture measurement is initiated whenever the device initiates an automatic moisture measurement.

11. A method of automatically initiating a moisture measurement in a moisture measuring device as set forth in claim 8 further including the steps of initiating a temperature compensation signal from a temperature sensor on the test cell to compensate the moisture measurement for different temperatures of the grain.

* * * * *